United States Patent [19]

Mosher et al.

[11] Patent Number: 5,342,762
[45] Date of Patent: Aug. 30, 1994

[54] FIBRONECTIN PURIFICATION VECTOR

[75] Inventors: Deane F. Mosher; Jane M. Sottile, both of Madison, Wis.

[73] Assignee: Wisconsin Alumni Research Foundation, Madison, Wis.

[21] Appl. No.: 637,250

[22] Filed: Jan. 3, 1991

[51] Int. Cl.$^5$ .................. C12N 15/11; C12N 15/66; C07K 3/12; C07K 3/18

[52] U.S. Cl. .................. 435/69.1; 435/172.3; 435/273; 435/320.1; 435/804; 435/814; 530/415; 530/417; 536/23.1; 536/24.2

[58] Field of Search ............ 435/69.1, 172.3, 320.1, 435/272, 273, 803, 814, 815; 530/413, 415, 417; 935/24, 48; 536/23.1, 24.2

[56] References Cited

PUBLICATIONS

F. Blumenstock, et al., 132 Meth. Enzym. 334–349 (1986).
D. Mosher, et al., 255 J. Bio. Chem. 1181–1188 (1980).
E. Barry, et al., 263 J. Bio. Chem. 10464–10469 (1988).
J. Vaughn, et al., 13 In Vitro 213–217 (1977).
D. Miller, et al., 8 Genetic Engineering: Principles & Methods 277–298 (1986).
Y. Matsuura, et al., 67 J. Gen. Virol. 1515–1529 (1986).
M. Summers, et al., Tex. Agri. Exp. Stn. Bull. 5–56 (1987).
K. Mullis, et al., 155 Meth. Enzyn. 335–350 (1987).
R. Patel, et al., 6 Embo. Journal 2565–2572 (1987).
L. Miller, et al., 42 Ann. Rev. Microbiol. 177–99 (1988).
T. Kunkel, et al., Recombinant DNA Methodology 587–601 (1989).
J. Sambrook, et al., Molecular Cloning, A Laboratory Manual, Cold Spring Harbor, 16.45–16.46 (1989).
T. Petersen, et al., 80 PNAS USA 137–141 (1983).
E. Ruoslahti, 57 Ann. Rev. Biochem. 375–413 (1988).
T. Petersen, et al., in Fibronectin 1–24 (1989).
K. Yamada, et al., in Fibronectin 47–121 (1989).
J. Thiery, et al., in Fibronectin 181–213 (1989).
R. Covin, in Fibronectin 213–254 (1989).
P. 204 of a Promega catalog showing the pGEM-4 vector; admitted prior art.
P. 220 of a Promega catalog showing the pGEM-72f(=) vector; admitted prior art.
Owens, R. J. et al., "Mapping the collagen–binding site of human fibronectin by expression in E. coli." EMBO (1986) 5:2825–2830.

Primary Examiner—Robert C. Wax
Assistant Examiner—Dian C. Jacobson
Attorney, Agent, or Firm—Quarles & Brady

[57] ABSTRACT

Recombinant protein purification vectors and methods for their use are disclosed. The vectors contain a DNA sequence coding for a gelatin binding region of fibronectin. The vectors express a foreign DNA sequence of interest fused to the fibronectin portion. Secretion signals on the fused product assist the product in being secreted from a production cell. The product can then be purified on a gelatin containing affinity column and digested with a protease such as trypsin to cleave the desired protein from the gelatin binding region. The vectors can also be designed to code for factor XIIIa cross liking sites and to have a chemically reactive cysteine residue.

5 Claims, 1 Drawing Sheet

FIBRONECTIN PURIFICATION VECTOR

This invention was made with U.S. government support awarded by the National Institute of Health (NIH), Grant #HL21644. The U.S. Government has certain rights in this invention.

This invention was made with U.S. government support awarded by the National Institutes Of Health (NIH) Grant Nos: HD07118, HL08136 and HL1644. The U.S. government has certain rights in this invention.

TECHNICAL FIELD

This invention relates to uses of a vector to synthesize and efficiently purify proteins of interest. More particularly, it relates to modifying genetic material coding for the amino-terminal part of fibronectin, and fusing DNA coding for proteins of interest to this part to help in the purification process.

BACKGROUND ART

Fibronectins are disulfide-bonded dimers found in vertebrates (e.g. mammals, birds, amphibians, fish, reptiles) that have been implicated in cell adhesion, wound healing, and embryogenesis. See E. Ruoslahti, 57 Ann. Rev. Biochem. 375–413 (1988); J. Thiery et al., in *Fibronectin* 181–212 (Academic Press 1989); R. Colvin, in *Fibronectin* 213–254 (Academic Press 1989). K. Yamada, in *Fibronectin* 47–121 (Academic Press 1989).

The majority of fibronectin consists of three types of repeating homology units. T. Petersen et al., 80 P.N.A.S. U.S.A. 137–141 (1983); T. Petersen et al., in *Fibronectin* 163–179 (Academic Press 1989). Type I repeats contain two intrachain disulfide bonds, and are present in the amino and carboxy-terminal regions of the molecule. Type II repeats are found only in a gelatin binding region of fibronectin, and also contain two intrachain disulfide bonds. There are also 15–17 copies of type III repeats, which are located in the central portion of the molecule, and lack intramolecular disulfide bonds.

Recent studies have shown that fibronectin becomes insolubilized into fibrils following binding to specific sites on the cell surface, termed matrix assembly sites. This binding is mediated by an amino-terminal 70 kDa fragment of fibronectin. The 70 kDa fragment contains nine copies of the type I repeat and two copies of the type II repeat. While much is known about the structure of fibronectins, the possibility of using all or part of a gene coding for the fibronectin gelatin binding region in a purification vector has not previously been suggested.

In connection with recombinant DNA technology it is often desirable to amplify large quantities of a vector (e.g. plasmid; phage), express proteinaceous material in a cell using the vector, cause the proteinaceous material to be secreted from the production cell into the surrounding media, and then purify the protein from the surrounding media. However, this process had not previously been optimized for expression of certain proteins. For example, while vectors had been created that efficiently express proteins, these proteins were often folded incorrectly, secreted inefficiently, and/or were difficult to separate from the surrounding media once secreted. This caused reduced yield, impurities in the final product, and/or required the use of overly expensive and time consuming purification techniques.

DISCLOSURE OF THE INVENTION

In one embodiment, the invention provides a recombinant protein purification vector. The vector has a nucleotide sequence coding for a portion of fibronectin that binds to gelatin. It also has a nucleotide sequence coding for a foreign desired proteinaceous material linked to the fibronectin coding nucleotide sequence such that when the foreign coding gene is expressed it produces a product which is the desired proteinaceous material fused to the fibronectin portion. Preferably, the vector also has a leader nucleotide sequence coding for a signal peptide that assists in translocation of the fused product into the secretory apparatus of eukaryotic cells.

In an especially preferred form, the vector also has nucleotide sequences coding for a factor XIIIa cross linking site and a protease cleavage site. When the product is formed it contains a factor XIIIa cross linking site and a protease cleavage site. The product can then be purified on a gelatin containing affinity chromatography column and trypsin digested to cleave the gelatin binding region from the desired protein (or desired protein/factor XIIIa cross linking site product). Another pass through the affinity column will then separate out proteins containing the gelatin binding region.

In another aspect, the invention provides a recombinant protein purification vector that has a vector backbone (usually a plasmid), a first nucleotide sequence coding for a portion of fibronectin that binds to gelatin, and a second nucleotide sequence coding for a signal peptide that assists in secretion of protein. The first and second nucleotide sequences are linked on the vector with a restriction enzyme site therebetween. The restriction enzyme site is not present on the vector backbone. This permits a foreign nucleotide sequence of interest to be ligated into the site and then expressed.

In yet another aspect, the invention provides a method of producing a desired proteinaceous material which involves using one of the above vectors to produce a product, and then using an affinity column containing gelatin to assist in purifying the product.

It has been discovered that DNA coding for a gelatin binding region of fibronectin can be expressed in a way so as to fuse it to foreign proteins of interest. The resulting product is designed so as to be secreted automatically from eukaryotic protein expression systems (e.g., insect cells, cos monkey cells). The fusion product then binds strongly and substantially uniquely to a gelatin containing affinity chromatography column, thereby yielding highly purified product.

The objects of the present invention therefore include providing methods and vectors of the above kind which permit proteins to be efficiently produced and purified. These and still other objects and advantages of the present invention will be apparent from the description which follows. The following embodiments do not represent the full scope of the invention. Rather, the invention may be employed in other embodiments. Reference is therefore to be made to the claims herein for interpreting the scope of the present invention.

BEST MODES FOR CARRYING OUT THE INVENTION

A. Materials

Figure 1:
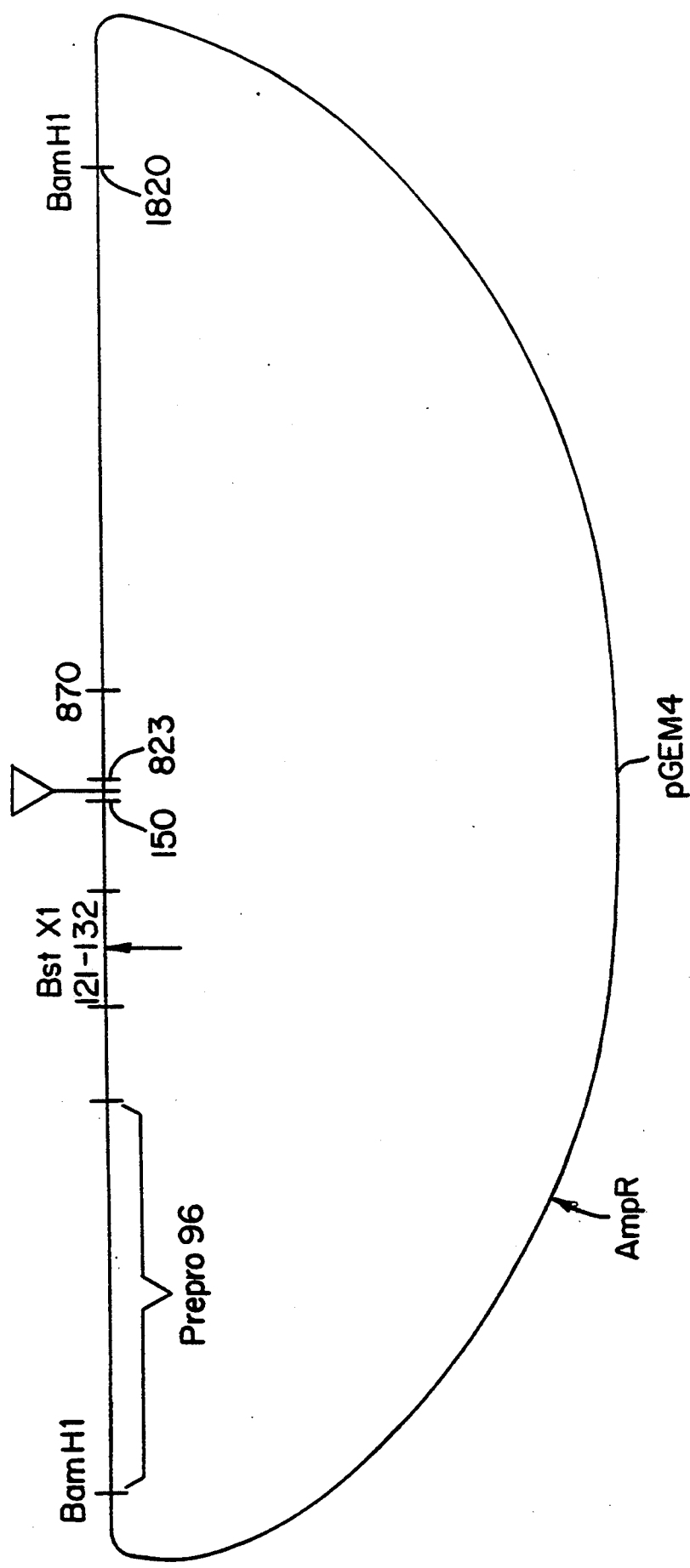
FIG. 1 schematically depicts the structure of the vector pGE-1/pGEM4.

BS70, a 1.8 kb 5' cDNA clone from rat fibronectin (S. Patel et al, 6 EMBO J. 2565–2572 (1987)) was obtained from J. Schwarzbauer (Princeton University, Princeton, N.J.). This clone is a HinfI-PstI fragment which contains 20 bp 5' to the ATG start codon and 1801 bp of coding sequence. This DNA (Fn571) encodes the first 571 amino acids of mature rat fibronectin, with a 5' 32 amino acid preprosequence. BamHI linkers were added to the 5' end of the DNA, and an XbaI-SalI linker containing an in frame stop codon to the 3' end of the DNA. After the addition of BamHI linkers to the 3' end of this construct, the DNA was cloned into the BamHI cloning site of a standard baculovirus replacement vector, pAcYMI. See Y. Matsuura et al., 67 J. Gen. virol. 1515–1529 (1986). See also L. Miller, 42 Ann. Rev. Microb. 177–199 (1988).

The insect cell line IPLB-SF-21 (J. Vaughn et al., 13 In Vitro 213–217 (1977)) was a gift from P. Freisen (University of Wisconsin, Madison). SF-21 cells were cultured in TC100 medium (Gibco, Grand Island, N.Y.) containing 10% fetal calf serum (HyClone, Logan, Utah), supplemented with 0.6 $\mu$g/ml amphotericin B (Gibco), 150 $\mu$g/ml Streptomycin-sulfate (Sigma, St. Louis, Mo.), and 99.7 U/ml penicillin (Sigma). Cells were grown to confluence (0.8–1.0 $\times$ 10$^6$ cells/ml) in monolayer culture at 27° C.

Nonrecombinant *Autographa californica* nuclear polyhedrosis virus (AcNPV) was a gift from P. Freisen. Viral DNA was prepared as described in D. Miller et al., 8 Genetic Engineering: Principles and Methods 277–298 (1986).

Normal human fibroblast strain TJ6F was isolated in this laboratory. Cells were maintained in DME:F12 (1:1) (Gibco) containing 10% fetal calf serum. Normal rat kidney cells (NRK clone 495; American Tissue Type Collection, CRL 1570) were cultured in DME containing 10% calf serum.

B. Production Of The Recombinant Virus Fn571/AcNPV pAcYMI containing Fn571 cDNA was cotransfected with AcNPV DNA into SF-21 cells with lipofectin (BRL, Gaithersburg, Md.) according to manufacturer's instructions. Recombinant viruses were selected and plaque purified three times as described in D. Miller et al., 8 Genetic Engineering: Principles and Methods 277–298 (1986); M. Summers et al., Tex. Agric. Exp. Stn. Bull, 5–56 (1987). SF-21 cells (10$^7$ cells/100 mm dish) were infected with recombinant virus at a multiplicity of infection of 10–20 in serum containing medium. After 24 hours, the medium was removed, the cells were gently washed three times with serum free TC100, then incubated with 5 ml/dish serum free TC100 for 48 hours at 27° C. The conditioned medium was collected and centrifuged at 2500 rpm for ten minutes at room temperature. The supernatant was decanted and stored frozen until use.

C. Protein Purification

Conditioned medium from Fn571 infected cells was applied to a gelatin-sepharose column (2 ml) at a flow rate of approximately 1 ml/min. The column was obtained by coupling gelatin to cyanogen bromide-activated agrose according to manufacture's instructions (Pharmacia). See also, F. Blumenstock et al., 132 Meth Enzym. 334–349 (1986) (gelatin sepharose). The column was washed with 0.15M NaCl, 20 mM Tris, pH 7.4 (Tris-buffered saline, TBS), then with 1M NaCl, 20 mM Tris, pH 7.4 prior to elution with 3M guanidine-HCl in TBS. The proteins were dialyzed against TBS, centrifuged to remove insoluble material, and stored at $-135°$ C.

Conditioned medium isolated from Fn571/AcNPV infected cells was also analyzed by SDS PAGE for the presence of recombinant protein. This medium contained a 68 kDa protein which was absent from the medium of cells infected with an irrelevant recombinant virus. The recombinant protein was present at a concentration of approximately 15–25 $\mu$g/ml, and was the only protein which specifically bound to gelatin-sepharose.

Immunoblotting of conditioned medium from infected cells showed that the 68 kDa protein cross-reacted with a polyclonal antibody to the 70 kDa fragment of human fibronectin. Medium from cells infected with an irrelevant recombinant virus did not contain any cross reacting proteins. This indicates that cells infected with Fn571/AcNPV produce a recombinant amino terminal fibronectin fragment.

The protein encoded by the Fn 571 construct is approximately 1–2 kDa smaller than the 70 kDa fragment produced by cathepsin digestion of human fibronectin. It should be noted in this regard that while rat fibronectin was used for the experiments described herein, gelatin binding regions of other vertebrate (e.g. mammalian) fibronectin DNA are also known. These should work in a similar manner.

D. Protease Digestion

The r70kDa protein (5 $\mu$g) was digested with N-tosyl-L-phenylalanine choloromethyl ketone (TPCK)-trypsin (Cooper Biomedical, Malvern, Pa.) at a final concentration of 1 $\mu$g/ml for three minutes. Digestions were stopped by the addition of five fold excess of soybean trypsin inhibitor (Sigma). This cleaved the molecule between the fifth and sixth type I repeats. D. Mosher et al., 255 J. Biol. Chem. 1181–1188 (1980). Analysis of trypsin cleavage products showed that a 27 kDa peptide was generated and that the signal and presumptive presequences had been cleaved from the r70kDa protein. It should be appreciated that a variety of other proteases cleave at or near the trypsin site and can be substituted for trypsin.

E. Construction Of An Expression Vector

Thus far we had used a baculovirus expression system to produce a r70kDa protein from the amino terminal region of fibronectin. This protein was synthesized in large amounts, was secreted from the cells, and was easily purified from the medium of infected cells by binding to a gelatin containing column. In vitro mutagenisis, described below, was used to express a mutant protein lacking the first through third type I homology units. This protein was also secreted in large amounts and easily purified.

We then decided to try to replace most of the 27 kDa amino-terminal region with a domain from other extracellular proteins. Such hybrid proteins could then be purified by affinity chromatography on gelatin and later the domains isolated after proteolysis.

FN571 was cloned into the BamHI cloning site of M13mp18 and used as a template for the first round of mutagenesis experiments. Oligonucleotide directed mutagenesis was performed according to T. Kunkel et al., in *Recombinant DNA Methodology* 587–601 (1989). Oligonucleotides were synthesized using an Applied Biosystems Automated DNA Synthesizer. An oligonucleotide designated GAP 1-3, TGGCTGTCAGTCAGAGCAAGGAGAAATGTTTTGATCACG, (SEQ ID NO:1) was used to delete the first through third type I homology units of fibronectin (bases 151–552; the A in the ATG start site is designated as 1). The fourth and fifth type I homology units (bases 553–882) were deleted from GAP 1-3/M13 template DNA using the GAP 1-5 primer, GGTGGCTGTCAGTCAGAGCAAGGTT-CTACAGAGTCTTCAGC (SEQ ID NO:2). The resulting GAP 1-5 phage was used to prepare single stranded DNA for the last round of mutagenesis. A 34-mer, CGTGCAGCCT-CCATCCCCGTGGGCTGTCAGTCAG, (SEQ ID NO:3) was designed to introduce a BstXI site (CCANNNNNNTGG, SEQ ID NO:4) after position 128. Underlined bases represent substitutions of the wild type sequence.

In addition to creation of the BstXI site, the codon for Val-44 was changed to a tryptophan codon (numbering per Petersen et al, infra) with 1 being the first amino acid of the mature protein. Single stranded DNA was sequenced through the AccI site at base 944 to confirm the mutations, and to verify that no other base changes were introduced. A 295 bp HindIII-AccI fragment from GE-1/M13 was then subcloned into FN571/pGEM72f that had been partially digested with HindIII/AccI to remove fibronectin sequences through the AccI site at base 944. pGEM72f was obtained from Promega. The resulting construct, GE-1/pGEM7Zf, contains a 672 bp deletion, and retains the intact coding region for the signal sequence, factor XIIIa site, trypsin site, and gelatin binding region of fibronectin.

Following digestion with BamHI, GE-1 was subcloned into pGEM4 (Promega, Madison, Wis.), which contains no BstX1 restriction enzyme site in the vector backbone, to yield pGE1/pGEM4. See FIG. 1. Plasmid pGE1/pGEM4 has been deposited at the American Type Culture Collection, Rockville, Md., U.S.A., in host DH5α cells, on Nov. 16, 1990 under the Budapest Treaty, with A.T.C.C. deposit #68480. The deposit will be made available as required by applicable patent laws. Such availability is not to be construed as a license under any patent.

The pGEM4 backbone has amp resistance and a single BamHI site. It has no BstX1 site. GE1 begins at the 5' end with 96 nucleotides (32 amino acids) of fibronectin preprosequence which regulates secretion of the protein from the cell. This is a leader signal peptide that allows translocation of the fused protein. Other leader sequences could be substituted for that of fibronectin if desired.

There are then 54 nucleotides of mature fibronectin in which a BstX1 restriction site has been created at nucleotides 121–132. The 54 nucleotides code for a factor XIIIa cross linking site. See E. Barry et al., 263 J. Biol. Chem. 10464–69 (1988). Nucleotides 151–822 of fibronectin DNA have been deleted. Then follows fibronectin nucleotides 823–1808 SEQ ID NO:8. Fibronectin nucleotides 823–1808 are disclosed at SEQ ID NO:8. Nucleotide 1 of SEQ ID NO:8 corresponds to nucleotdie 823 in the fibronectin mRNA sequence. The trypsin cleavage site coding begins at nucleotide 870. The gelatin-binding region is coded for by nucleotides 3' of 870.

F. Insertion Of Genes In BstX1.

As an example of inserting a gene of interest in the BstX1 site, a gene coding for another part of fibronectin can be inserted in the purification vector. It will be appreciated that by similar techniques other DNA coding for proteins of interest can be expressed and purified. Eukaryotic genes (or parts of genes) coding for blood coagulation factor IX, the protease domain of factor IX, epidermal growth factor domains, thrombospondin, vitronectin, or kininogens are preferred, but numerous other genes (or parts of genes) may also be inserted. The term "foreign" in the claims therefore is intended to mean any non-fibronectin protein.

As an example, polymerase chain reaction (PCR) primers can be synthesized to amplify fibronectin cDNA encoding the 12th type I homology unit (I-12): primer A (antisense): 5'-GGCCACGGGGATGGG-CCAGTGGTACCATCGGG-3', (SEQ ID NO:5) primer B (sense): 5'-GGCCATCCCCGTGG-GCAACGTGTTATGACGAC-3'(SEQ ID NO:6). Underlined sequences represent bases introduced at the 5' ends of the fibronectin DNA to create a BstXI site for in-frame cloning into GE-1/pGEM4.

PCR can be performed according to established procedures such as those of K. Mullis et al., 155 Meth. Enzym. 335–350 (1987), using Taq polymerase. A 3' fibronectin cDNA clone, BDP+7 (a gift from J. Schwarzbauer, Princeton University, Princeton, N.J.) can be used as a template for amplification. Amplified DNA (198 bp) can be gel purified, digested with BstXI, then cloned into the BstXI cloning site of GE-1/pGEM4. Following digestion with BamHI, GE-1 can be subcloned into suitable expression cells such as the COS cell expression vector, pSVL (Pharmacia, Piscataway, N.J.), the baculovirus expression vector, pAcYM1 (Y. Matsuura et al., 67 J. Gen. Virol. 1515–1529 (1986)), or BL1 (Invitrogen, San Diego, Calif.).

G. Expression Cells.

As an example, DNA can be transfected into COS-1 cells (a gift from D. Greenspan, University of Wisconsin, Madison) using DEAE-dextran (Pharmacia). as described in J. Sambrook et al., Molecular Cloning: A Laboratory Manual (2nd Ed. Cold Spring Harbor) 16.45–16.46 (1989). Cultures can be labelled with Tran $^{35}$S label (50 UCi/ml; ICN, Irvine, Calif.) 40–48 hours after tranfection in serum free MEM lacking methionine and cysteine. Conditioned medium can be harvested after 20–24 hours, and applied to a 1 ml gelatin-agarose column at a flow rate of 0.5 ml/minute. After washing sequentially with phosphate buffered saline (PBS) pH 7.4, 1M NaCl1/10 mM tris, pH 7.4, and PBS, proteins can be eluted from the column with 3M guanidine-HCl in tris buffered saline (TBS), pH 7.4. Fractions (0.5 ml) can be counted on a scintillation counter, pooled, and dialyzed against TBS. The dialysate can be recovered, spun at 2500 rpm for ten minutes to remove insoluble materials, and recounted.

I-12/GE-1 can, in the alternative, be expressed in insect cells using a baculovirus expression system as described above. Conditioned medium can be harvested from infected cells and purified by a gelatin sepharose affinity chromatography, as described previously.

H. Trypsin Cleavage.

I-12 can be separated from the gelatin binding domain of fibronectin by mild digestion with 1 μg/ml trypsin for three minutes at room temperature as described above. The gelatin-binding 40 kDa fragment, as well as any undigested protein, can be separated from the I-12 protein by a second round of gelatin chromatography.

Other Variants

It should be appreciated that many other vectors can be designed with other unique ligation sites and the fibronectin gene. Also, while a gelatin-agarose or gelatin-Sepharose column is preferable, other affinity columns containing gelatin should also work.

While the protein can be expressed and purified bound to the gelatin binding region of fibronectin, it is preferred that after initially using the column that the gelatin binding region be cleaved off using trypsin or another protease. It should also be appreciated that the region around the BstX1 site after cleavage codes for an amino acid sequence beginning:

pEAQQIVQPPSPWxxx...xxxPSPWAVSQSKVLQSASAGSGSFTDVR...(SEQ ID NO:7) where pE=pyroglutamic acid (first amino acid of the mature protein), Q=target for modification by factor XIIIa, W=change from the wild type sequence, xxx...xxx=the sequence of the inserted foreign amino acids, PSPW=an extra sequence introduced by the 3' half of the BstXI site, KV=junction between gapped out natural sequences, S=residues that can be mutated to C and become targets for modification with cysteine-specific reagents if desired, and R=new carboxyl terminal after trypsinization. Thus, the protein can preferably be produced with a factor XIIIa cross linking site. This is very desirable because if the protein is known to bind to a protein on a cell surface (e.g. a receptor), the protein might be cross-linked to the receptor by factor XIIIa, thereby providing a means of identifying the receptor.

Industrial Applicability

The present invention provides a means to efficiently produce and purify large quantities of a desired protein.

---

We claim:

1. A recombinant protein purification vector, comprising:
    a nucleotide sequence coding for a portion of fibronectin that binds to gelatin, wherein the nucleotide sequence is present in nucleotides 823–1808 of the fibronectin gene according to SEQ ID NO: 8; and
    a nucleotide sequence coding for a foreign protein linked to the fibronectin coding nucleotide sequence such that when the foreign protein coding nucleotide sequence is expressed it produces a product which is the foreign protein fused to said fibronectin protein wherein the foreign protein coding nucleotide sequence is upstream from said fibronectin coding nucleotide sequence and wherein there is a nucleotide sequence coding for a protease cleavage site between the foreign protein coding nucleotide sequence and the fibronectin protein nucleotide sequence, and wherein the protease cleavage site is one that naturally occurs in fibronectin protein; and wherein the vector further comprises a leader nucleotide sequence coding for a fibronectin pre-prosequence upstream from the nucleotide sequence coding for a foreign protein.

2. The vector of claim 1, wherein the vector further comprises a leader nucleotide sequence coding for a fibronectin pre-prosequence upstream from the nucleotide sequence coding for a foreign protein.

3. A method of producing a desired protein comprising using the vector of claim 1 to produce said protein product by inserting the vector of claim 1 into a suitable host cell and allowing the claim 1 protein to be expressed, and then using an affinity column containing gelatin to assist in purifying the product.

4. The method of claim 3, further comprising the steps of digesting the product with a protease after the use of an affinity column containing gelatin and then subjecting the digested product to an additional chromatography purification.

5. A recombinant protein purification vector, comprising:
a vector backbone;
a first nucleotide sequence coding for a portion of fibronectin that binds to gelatin, wherein the nucleotide sequence is present in nucleotides 823–1808 of the fibronectin gene according to SEQ ID NO:8;
a second nucleotide sequence coding for a protease cleavage site wherein the protease cleavage site is one that naturally occurs in fibronectin protein; and
a restriction enzyme site, said restriction enzyme site not being present on the vector backbone, wherein the first nucleotide sequence is downstream from the restriction site, and wherein the second nucleotide sequence is between the restriction site and at least part of the first nucleotide sequence, and wherein the vector further comprises a leader sequence coding for a fibronectin pre-prosequence that is positioned upstream from the restriction site.

* * * * *

UNITED STATES PATENT AND TRADEMARK OFFICE
CERTIFICATE OF CORRECTION

PATENT NO. : 5,342,762

DATED : August 30, 1994

INVENTOR(S) : Deane F. Mosher, et al

Page 1 of 2

It is certified that error appears in the above-indentified patent and that said Letters Patent is hereby corrected as shown below:

Column 5, lines 9 and 10:

"CGTGCAGCCTCCATCCCCGTGGGCTGTCAGTCAG" s/b
--CGTGCAGCCTCCATCCCCGTGGGCTGTCAGTCAG--.

Column 5, line 55: please delete "SEQ ID NO:8"

Column 6, lines 9 - 12:

"5' GGCCACGGGGATGGGCCAGTGGTACCATCGGG 3', (SEQ ID NO:5) primer B (sense): 5'- GGCCATCCCCGTGGGCAACGTGTTATGACGAC-3'. s/b
-- 5'-GGCCATCCCCGTGGGCAACGTGTTATGACGAC-3'.(SEQ ID NO:5) primer B (sense): 5'-GGCCATCCCCGTGGGCAACGTGTTATGACGAC 3'--.

UNITED STATES PATENT AND TRADEMARK OFFICE
CERTIFICATE OF CORRECTION

PATENT NO. : 5,342,762
DATED : August 30, 1994
INVENTOR(S) : Deane F. Mosher et al It is certified that error appears in the above-indentified patent and that said Letters Patent is hereby corrected as shown below:

Column 6, line 43:  "NaCl1/10 mM" s/b --NaCl/10 mM--.

Column 12, Row 26:

"GTTCTACAGA GTGCTTCAGC TGGATCTGGC TCCTTCACAG ATGTCCGAAC AGCTATTTAC 60" s/b
--GTTCTACAGA GTGCTTCAGC TGGATCTGGC TCCTTCACAG ATGTCCGAAC AGCTATTTAC   60--.

Signed and Sealed this

Thirty-first Day of January, 1995

Attest:

BRUCE LEHMAN

Attesting Officer  Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 39 bases
( B ) TYPE: nucleic acid
( C ) STRANDEDNESS: single
( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:1:

TGGCTGTCAG TCAGAGCAAG GAGAAATGTT TTGATCACG 39

( 2 ) INFORMATION FOR SEQ ID NO:2:

( i ) SEQUENCE CHARACTERISTICS:
( A ) LENGTH: 41 bases
( B ) TYPE: nucleic acid
( C ) STRANDEDNESS: single
( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:2:

GGTGGCTGTC AGTCAGAGCA AGGTTCTACA GAGTCTTCAG C 41

( 2 ) INFORMATION FOR SEQ ID NO:3:

( i ) SEQUENCE CHARACTERISTICS:
( A ) LENGTH: 34 bases
( B ) TYPE: nucleic acid
( C ) STRANDEDNESS: single
( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:3:

CGTGCAGCCT CCATCCCCGT GGGCTGTCAG TCAG 34

( 2 ) INFORMATION FOR SEQ ID NO:4:

( i ) SEQUENCE CHARACTERISTICS:
      ( A ) LENGTH: 12 bases
      ( B ) TYPE: nucleic acid
      ( C ) STRANDEDNESS: single
      ( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:4:

CCANNNNNNT GG                                                  1 2

( 2 ) INFORMATION FOR SEQ ID NO:5:

( i ) SEQUENCE CHARACTERISTICS:
      ( A ) LENGTH: 32 bases
      ( B ) TYPE: nucleic acid
      ( C ) STRANDEDNESS: single
      ( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:5:

GGCCACGGGG ATGGGCCAGT GGTACCATCG GG                            3 2

( 2 ) INFORMATION FOR SEQ ID NO:6:

( i ) SEQUENCE CHARACTERISTICS:
      ( A ) LENGTH: 32 bases
      ( B ) TYPE: nucleic acid
      ( C ) STRANDEDNESS: single
      ( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:6:

GGCCATCCCC GTGGGCAACG TGTTATGACG AC                            3 2

( 2 ) INFORMATION FOR SEQ ID NO:7:

( i ) SEQUENCE CHARACTERISTICS:
      ( A ) LENGTH: 44 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
      ( A ) NAME/KEY: Modified-site
      ( B ) LOCATION: 1..2
      ( D ) OTHER INFORMATION: /label=Modification
            / note="The first residue is pyroglutamic acid."

( i x ) FEATURE:
      ( A ) NAME/KEY: Modified-site (B) LOCATION: 13..18
(D) OTHER INFORMATION: /label=insertion
/ note="The sequence Xaa Xaa
Xaa Xaa Xaa
Xaa indicates the position of
the
inserted foreign amino acid."

(xi) SEQUENCE DESCRIPTION: SEQ ID NO:7:

Xaa Ala Gln Gln Ile Val Gln Pro Pro Ser Pro Trp Xaa Xaa Xaa Xaa
1             5                 10                  15

Xaa Xaa Pro Ser Pro Trp Ala Val Ser Gln Ser Lys Val Leu Gln Ser
         20                  25                  30

Ala Ser Ala Gly Ser Gly Ser Phe Thr Asp Val Arg
         35                  40

(2) INFORMATION FOR SEQ ID NO:8:

(i) SEQUENCE CHARACTERISTICS:
    (A) LENGTH: 986 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (vi) ORIGINAL SOURCE:
    (A) ORGANISM: Rattus norvegicus (xi) SEQUENCE DESCRIPTION: SEQ ID NO:8:

```
GTTCTACAGA GTGCTTCAGC TGGATCTGGC TCCTTCACAG ATGTCCGAAC AGCTATTTAC   60
CAACCCCAGA CCCACCCCCA GCCCGCACCG TACGGCCACT GTGTCACAGA CAGCGGTGTG  120
GTCTACTCTG TGGGAATGCA GTGGCTGAAG TCTCAAGGAG ACAAGCAGAT GCTGTGCACT  180
TGCCTGGGCA ATGGCGTCAG CTGCCAGGAG ACAGCTGTGA CCCAGACTTA CGGTGGCAAC  240
TCAAACGGGG AGCCCTGTGT TCTCCCGTTT CACTACAACG GTAGGACCTT CTACTCCTGC  300
ACCACCGAAG GGCGGCAAGA CGGACATCTG TGGTGTAGCA CAACTTCAAA TTATGAACAA  360
GACCAGAAGT ATTCTTTCTG CACAGACCAC GCGGTTTTGG TTCAGACTCG AGGTGGGAAT  420
TCCAATGGTG CCTTGTGCCA CTTCCCCTTC CTGTACAGCA ACCGGAATTA CAGCGACTGT  480
ACTTCTGAGG GTAGGCGGGA CAACATGAAA TGGTGCGGCA CCACCCAGAA CTACGATGCC  540
GATCAGAAGT TTGGATTCTG CCCAATGGCT GCCCATGAGG AGATCTGCAC GACCAACGAA  600
GGGGTCATGT ATCGCATTGG GGACCAGTGG GATAAGCAGC ATGACCTGGG CCACATGATG  660
AGGTGCACGT GTGTTGGGAA CGGCCGTGGA CAATGGGCCT GCATCCCCTA CTCCCAGCTC  720
CGAGATCAGT GCATCGTTGA TGACATTACT TACAACGTCA ACGACACGTT CCACAAGCGT  780
CACGAGGAGG GACATATGCT GAACTGTACC TGCTTCGGTC AGGGCCGGGG CAGATGGAAA  840
TGTGACCCCA TCGACCGATG CCAAGATTCA GAGACCCGGA CATTTTACCA GATTGGTGAC  900
TCCTGGGAGA AGTTTGTGCA TGGTGTCAGA TACCAGTGTT ACTGTTACGG CCGTGGCATT  960
GGGGAGTGGC ACTGCCAGCC TCTGCA                                      986
```